US012643874B2

(12) United States Patent
Panchal et al.

(10) Patent No.: US 12,643,874 B2
(45) Date of Patent: Jun. 2, 2026

(54) PROCESS FOR PREPARATION OF ARTHROPODICIDAL ANTHRANILAMIDE COMPOUNDS

(71) Applicant: UPL LTD, Mumbai (IN)

(72) Inventors: Digish Manubhai Panchal, Mumbai (IN); Rakesh Bhulabhai Patel, Mumbai (IN)

(73) Assignee: UPL LTD, Mumbai (IN)

( * ) Notice: Subject to any disclaimer, the term of this patent is extended or adjusted under 35 U.S.C. 154(b) by 820 days.

(21) Appl. No.: 17/798,970

(22) PCT Filed: Feb. 11, 2021

(86) PCT No.: PCT/IB2021/051103

§ 371 (c)(1),
(2) Date: Aug. 11, 2022

(87) PCT Pub. No.: WO2021/161200

PCT Pub. Date: Aug. 19, 2021

(65) Prior Publication Data

US 2023/0088326 A1 Mar. 23, 2023

(30) Foreign Application Priority Data

Feb. 12, 2020 (IN) ............................ 202021006036

(51) Int. Cl.
*C07D 401/04* (2006.01)

(52) U.S. Cl.
CPC .................................. *C07D 401/04* (2013.01)

(58) Field of Classification Search
CPC .................................................... C07D 401/04
USPC ...................................................... 546/275.4
See application file for complete search history.

(56) References Cited

U.S. PATENT DOCUMENTS

| | | | |
|---|---|---|---|
| 7,232,836 | B2 | 6/2007 | Lahm et al. |
| 7,247,647 | B2 | 7/2007 | Hughes et al. |
| 2014/0235865 | A1 | 8/2014 | Pazenok et al. |

FOREIGN PATENT DOCUMENTS

| | | | |
|---|---|---|---|
| CN | 101298451 | B | 1/2013 |
| EP | 3141545 | A1 | 3/2017 |
| WO | 2019207595 | A1 | 10/2019 |
| WO | 2019224678 | A1 | 11/2019 |

OTHER PUBLICATIONS

International Search Report and Written Opinion for International Application PCT/IB2021/051103; International Filing Date: Feb. 11, 2021; Date of Mailing: May 7, 2021; 14 pages.

*Primary Examiner* — Kahsay Habte
(74) *Attorney, Agent, or Firm* — CANTOR COLBURN LLP

(57) ABSTRACT

The present invention provides a process for preparation of arthropodicidal anthranilamide compounds. The present invention further relates to one pot process for preparation of anthranilamide compounds.

10 Claims, No Drawings

PROCESS FOR PREPARATION OF ARTHROPODICIDAL ANTHRANILAMIDE COMPOUNDS

CROSS REFERENCE TO RELATED APPLICATIONS

This application is a National Stage application of PCT/IB2021/051103, filed Feb. 11, 2021, which claims the benefit of priority to Indian Patent Application number 202021006036, filed Feb. 12, 2020, both of which are incorporated by reference in their entirety herein.

FIELD OF INVENTION

The present invention relates to a process for preparation of arthropodicidal anthranilamide compounds. The present invention further relates to one pot process for preparation of anthranilamide compounds.

BACKGROUND OF THE INVENTION

Effective control of insect pest such as arthropods is essential for crop safety. Arthropods are an important class of pests which cause huge damage to crop and household every year around the world. Anthranilamides are a new class of compounds with extremely potent insecticidal activity. These nitrogen-containing aromatic compounds selectively act on targeted ryanodine receptors which form calcium ion channels which are responsible for muscle function in insects.

Examples of insecticidal anthranilamides are cyantraniliprole, chlorantraniliprole, cyclaniliprole, tetrachlorantraniliprole and tetraniliprole. Chlorantraniliprole is a highly potent and selective activator of insect ryanodine receptor with exceptional activity on a broad range of Lepidoptera. It controls a wide range of chewing pests (primarily Lepidoptera, but also some Coleoptera, Diptera and Isoptera species) in a broad range of crops, including fruit, vegetables, vines, cotton, sugar cane, rice and grass.

The following disclosure and description of the prior art is intended to present the invention in an appropriate technical context and allows its significance to be suitably considered and appreciated. Unless clearly indicated to the contrary, the reference to any prior art in this specification should not be construed as an expressed or implied admission that such art is widely known or forms part of common general knowledge in the field.

U.S. Pat. No. 7,247,647 disclose a compound of Formula 1, an N-oxide or a salt thereof and synthesis thereof.

Formula I

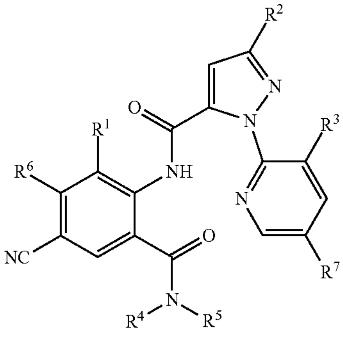

U.S. Pat. No. 7,232,836 discloses anthranilamides compounds of the following formula and process for preparation thereof.

Formula V

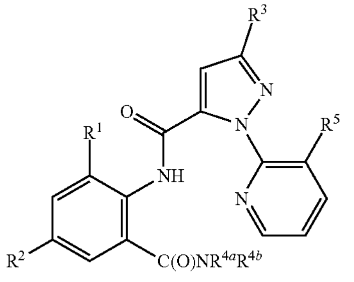

U.S. Pat. No. 7,232,836 teaches a process for preparation of chlorantraniliprole which involves the reaction as shown in below reaction scheme.

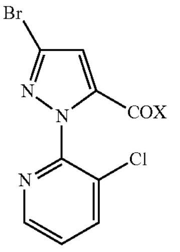

Formula I

+

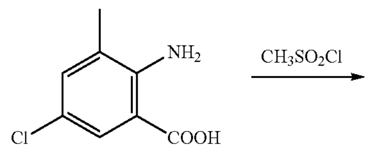

Formula II

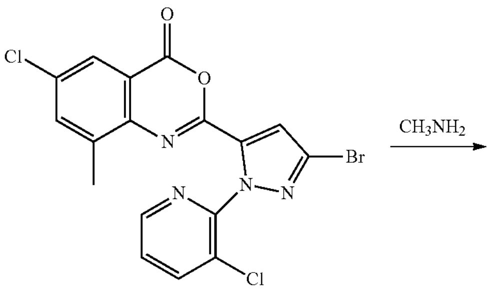

Formula III

-continued

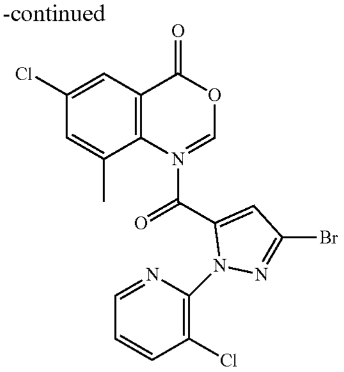

Chlorantraniliprole (Formula IV)

In the above preparation processes, the intermediate compounds in each step need to be isolated and purified by column chromatography, which is difficult to meet the demand for industrial mass production. It is necessary to obtain compounds in highly pure form that is free from unwanted impurities. These impurities may be formed at various intermediate stages of the process. Inventors of the present invention observed that the intermediate compound (Formula III) is not physically stable enough to undergo appropriate purification. It has been further noted that impure intermediate compound leads to impure product which is not suitable for the intended use. Further, the above process involves use of methane sulfonyl chloride in large excess that will lead to large amount of waste generation as well as handling of effluent become cumbersome. The above said drawbacks make the process unviable on commercial scale.

CN101298451 discloses benzamide compounds represented by following formula and referred herein as Formula V and synthesis process thereof.

Formula V

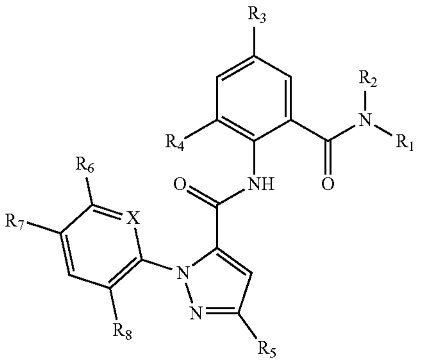

There exists a need to develop an alternative, simple, cost-effective, reproducible, commercially viable and an efficient process for preparation of anthranilamide compounds with high yield, simple operation, which is environmentally friendly and suitable for industrial production.

OBJECTS OF THE INVENTION

It is an object of the present invention to provide a simple, cost-effective, reproducible, commercially viable and industrially feasible process fora process for preparation of anthranilamide compounds or salts, isomers, N-oxides and derivatives thereof.

It is another object of the present invention to provide a process for the preparation of chlorantraniliprole.

It is another object of the present invention to provide a simple, an environmentally friendly and cost-effective one pot process for the preparation of chlorantraniliprole.

SUMMARY OF THE INVENTION

In an aspect the present invention provides a process for the preparation of anthranilamide compounds or salts, isomers, N-oxides and derivatives thereof.

In another aspect the present invention provides a process for preparation of anthranilamide compounds of Formula IX.

Formula IX

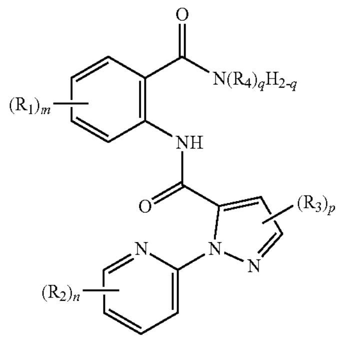

In another aspect the present invention provides a one pot process for the preparation of a compound of Formula (XIII)

Formula XIII

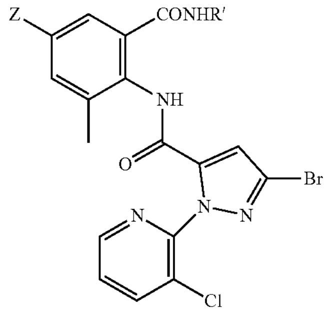

In another aspect the present invention provides a process for the preparation of chlorantraniliprole.

In another aspect the present invention provides a one pot process for the preparation of chlorantraniliprole.

In another aspect the present invention provides a one pot process for the preparation of chlorantraniliprole in the absence of base.

In another aspect the present invention provides a process comprising preparation of anthranilamides of Formula (XIII):

a) reacting compound of Formula (X) wherein Y is a halogen, with a compound of Formula (XI) wherein Z is halogen or CN and R is a lower alkyl group optionally in the presence of a weak base to obtain compound of Formula (XII), wherein Z and R are as defined above and

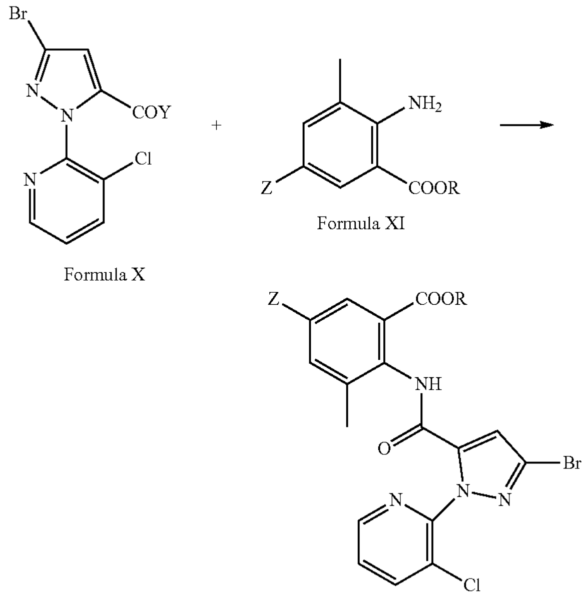

Formula X Formula XI Formula XII b) reacting compound of Formula (XII) with alkyl amine of formula R'$NH_2$ wherein R' is selected from unsubstituted or substituted linear or branched ($C_1$-$C_{10}$)alkyl or cycloalkyl, heterocyclic unsubstituted or substituted with halogen, cyano, amino, hydroxyl to obtain a compound of Formula (XIII).

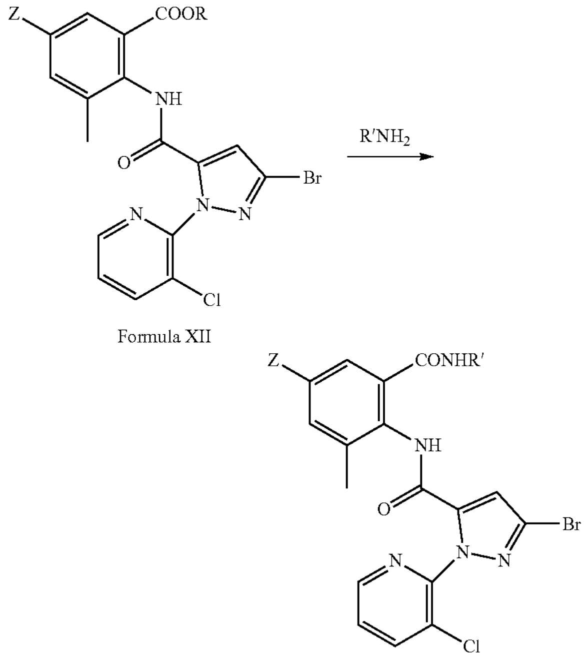

Formula XII Formula XIII

DETAILED DESCRIPTION OF THE INVENTION

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention.

Listed below are definitions of various terms used to describe the compounds of the present invention. These definitions apply to the terms as they are used throughout the specification (unless they are otherwise limited in specific instances) either individually or as part of a larger group. They should not be interpreted in the literal sense. They are not general definitions and are relevant only for this application.

It must be noted that, as used in this specification, the singular forms "a," "an" and "the" include plural referents unless the content clearly dictates otherwise. The terms "preferred" and "preferably" refer to embodiments of the invention that may afford certain benefits, under certain circumstances.

As used herein, the terms "comprising" "including," "having," "containing," "involving," and the like are to be understood to be open-ended, i.e., to mean including but not limited to.

In any aspect or embodiment described herein below, the phrase comprising may be replaced by the phrases "consisting of" or "consisting essentially of" or "consisting substantially of".

In these aspects or embodiment, the combination or composition described includes or comprises or consists of or consists essentially of or consists substantially of the specific components or steps of process recited therein.

Unless stated otherwise, the term "alkyl" includes unsubstituted alkyl groups as well as alkyl groups, which are substituted by one or more different substituents. In preferred embodiments, a straight chain or branched chain alkyl has 1 to 10 carbon atoms (($C_1$-$C_{10}$) alkyl). Likewise, preferred cycloalkyls have from 3-10 carbon atoms in their ring structure, and more preferably have 5, 6 or 7 carbons in the ring structure. Examples of alkyl residues containing from 1 to 20 carbon atoms are: methyl, ethyl, propyl, butyl, pentyl, hexyl, heptyl, octyl, nonyl, decyl, undecyl, dodecyl, tetradecyl, hexadecyl, octadecyl and eicosyl, the n-isomers of all these residues, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, or tert-butyl.

The term "heterocyclic" refers to a stable 3 to 7 membered ring radical which consists of carbon atoms and from one to three heteroatoms selected from the group consisting of nitrogen, oxygen and sulfur. In addition, the nitrogen atom may be optionally quaternized; examples of such heterocyclic ring radicals include, but are not limited to, thiazolidinyl, pyrrolidinyl, tetrahydrofuryl, morpholinyl, pyranyl, dioxolanyl and the like.

Unless stated otherwise, the heterocyclic groups can be unsubstituted or substituted with one or more (e.g., up to 3), identical or different, substituents. Examples of substituents for the ring carbon and ring nitrogen atoms are hydroxy, halogen, carboxyl, alkoxycarbonyl, cyano, amino, nitro, oxo (=O), alkyl, alkoxy, aryl, aralkyl, heteroaryl and heterocyclo.

The term "halogen" refers to radicals of fluorine, chlorine, bromine or iodine.

The term "amino" refers to the group —$NH_2$ which may be optionally substituted with alkoxycarbonyl, amino, alkyl, aryl, aralkyl, heteroaryl and heterocyclo wherein the terms alkyl, aryl, aralkyl, heteroaryl and heterocyclo are as defined herein above.

It will be understood that "substitution" or "substituted with" includes the implicit proviso that such substitution is in accordance with the permitted valence of the substituted atom and the substituent, as well as results in a stable compound, which does not readily undergo transformation such as by rearrangement, cyclization, elimination, etc.

Inventors of the present invention have developed an improved process that addresses the problems associated with the processes reported in the prior art. The inventors of the present inventors reported a direct method to prepare anthranilamide compounds which has not been explicitly reported.

Inventors of the present invention have developed an improved process that addresses the problems associated with the processes reported in the art.

Accordingly, the present invention provides a simple, scalable and economically viable process that provides anthranilamide compounds in high yields and purity. The present process is simple, efficient, cost effective, environmentally friendly and commercially scalable for large scale operations.

In an aspect the present inventio provide a one pot process for the preparation of anthranilamide compounds.

The "one-pot process" for preparing anthranilamide compounds is simple and does not need isolation of intermediates with a shortened production cycle and a reduced equipment requirement, and thus it is more suitable for industrial production.

In an aspect the present invention provides a process for the preparation of anthranilamide compounds of formula (IX).

In an embodiment, the process for preparation of anthranilamide compound of Formula (IX) comprises reaction of compound of Formula (VI) with a compound of Formula (VII) to obtain compound of Formula (VIII) and reacting the compound of Formula (VIII) with an alkyl amine of formula $R_4$—$NH_{2-q}$ to obtain compound of Formula (IX) wherein X=a halogen, R=a lower alkyl group, $R_1$, $R_2$ and $R_3$ are independently a hydrogen, halogen, cyano, amino, N-thio derivatives, hydroxyl, unsubstituted or substituted linear or branched ($C_1$-$C_{10}$)alkyl or cycloalkyl, heterocyclic unsubstituted or substituted with halogen, cyano, amino, hydroxyl or linear or branched ($C_1$-$C_{10}$) alkyl and $R_4$ is selected from unsubstituted or substituted linear or branched ($C_1$-$C_{10}$)alkyl or cycloalkyl, heterocyclic unsubstituted or substituted with halogen, cyano, amino, hydroxyl or linear or branched ($C_1$-$C_{10}$) alkyl and wherein m and n can be 0, 1, 2, or 3, p can be 0, 1, or 2 and q can be 0 or 1.

In an embodiment the process is represented in below scheme.

Scheme 1

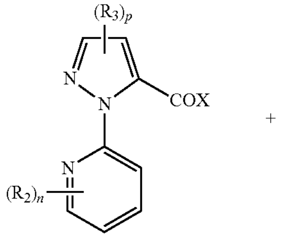

Formula VI

-continued

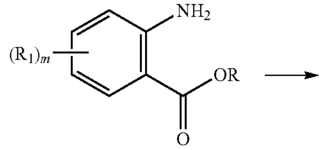

Formula VII

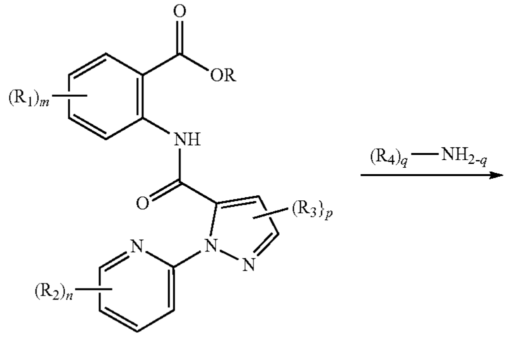

Formula VIII

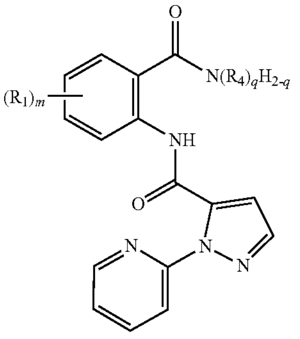

Formula IX

Accordingly the present invention provides a one pot process for the preparation of anthranilamides of Formula (IX) said process comprising reacting compound of Formula (VI) with a compound of Formula (VII) to obtain compound of Formula (VIII) and reacting compound of Formula (VIII) with an alkyl amine of formula $(R_4)_q$—$NH_{2-q}$ to obtain said compound of Formula (IX) wherein X is a halogen, R is a lower alkyl group, $R_1$, $R_2$ and $R_3$ are independently a hydrogen, halogen, cyano, amino, N-thio derivatives, hydroxyl, unsubstituted or substituted linear or branched ($C_1$-$C_{10}$)alkyl or cycloalkyl, heterocyclic unsubstituted or substituted with halogen, cyano, amino, hydorxyl or linear or branched ($C_1$-$C_{10}$) alkyl and $R_4$ is selected from unsubstituted or substituted linear or branched ($C_1$-$C_{10}$)alkyl or cycloalkyl, heterocyclic unsubstituted or substituted with halogen, cyano, amino, hydorxyl or linear or branched ($C_1$-$C_{10}$) alkyl and wherein m and n are 0, 1, 2, or 3, p is 0, 1, or 2 and q is 0 or 1. The one pot process is represented in the below scheme.

Scheme 2

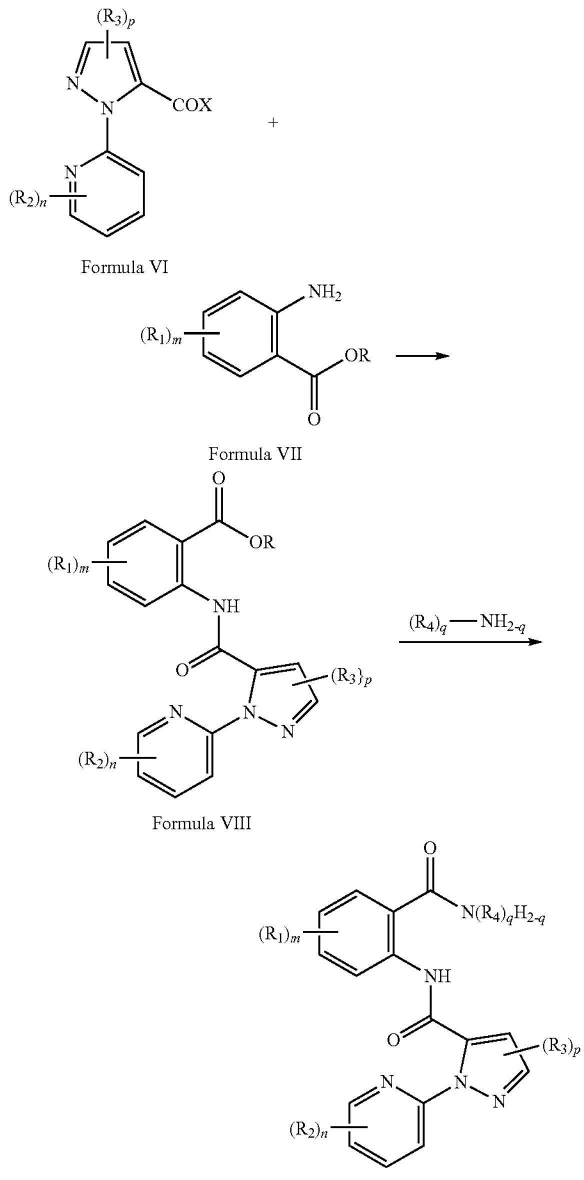

Formula VI

Formula VII

Formula VIII

Formula IX

In a preferred embodiment the process for preparation of anthranilamides of Formula (IX) according to the present invention is performed in one pot.

In a preferred embodiment the one pot process is carried out in the absence of a base.

The anthranilamide of Formula (IX) obtained by the "one-pot process" is pure and suitable for intended agriculture use. The overall yield of the "one-pot process" for preparing anthranilamide of Formula (IX) is higher. The purity of the obtained compound (IX) is more than 95% by HPLC.

In another embodiment the present invention provides a process for preparation of anthranilamide of Formula (IX) wherein Riis a lower alkyl, halogen or cyano, $R_2$ is halogen, $R_3$ is halogen, $R_4$ is a lower alkyl or alkyl cycloalkyl, m is 2, n is 1, p is 1, and q is 1.

In an embodiment the invention provides a process for preparation of anthranilamide compound of Formula (IX) wherein $R_1$ is $CH_3$, bromine and/or chlorine, $R_2$ is chlorine, $R_3$ is bromine and $R_4$ is $CH_3$.

In an embodiment the invention provides a process for preparation of anthranilamide compound of Formula (IX) wherein $R_1$ is $CH_3$ and/or cyano, $R_2$ is chlorine, $R_3$ is bromine and $R_4$ is $CH_3$.

In an embodiment post-reaction treatment of formula (VIII) is avoided.

In an embodiment the compound of formula (VIII) is not isolated.

In an embodiment the process according to the present invention provides a compound of Formula (VIII) wherein X is a halogen preferably chlorine, R is a lower alkyl group, $R_1$, $R_2$ and $R_3$ are independently a hydrogen, halogen or cyano.

In an embodiment the process according to the present invention provides a compound of formula (VIII) wherein $R_1$ is $CH_3$ and chlorine, $R_2$ is chlorine, $R_3$ is bromine, $R_4$ is $CH_3$ and m is 2.

In an embodiment the process according to the present invention provides a compound of Formula (VIII) wherein X is chlorine, R is $CH_3$, $R_1$ is $CH_3$ and cyano, $R_2$ is chlorine, $R_3$ is bromine and m is 2.

In an embodiment compound of formula (VIII) product is subjected to reaction with an alkyl amine of formula $(R_4)_q$—$NH_{2-q}$ without isolation.

In an embodiment the reaction is carried out by reacting a compound of formula (VIII) with an alkyl amine of formula $(R_4)_q$—$NH_2$ wherein $R_4$ is selected from unsubstituted or substituted linear or branched ($C_1$-$C_{10}$)alkyl or cycloalkyl, heterocyclic unsubstituted or substituted with halogen, cyano, amino, hydroxyl or linear or branched ($C_1$-$C_{10}$) alkyl wherein q is 0 or 1.

In an embodiment the process is carried out in an organic solvent.

In an embodiment the process is carried out in an organic solvent such as halogenated solvent, hydrocarbon solvent, ether or acetonitrile.

The compounds of Formula (VI) and Formula (VII) are prepared by methods known in the art.

In a preferred embodiment the compounds of Formula (VI) is 3-Bromo-1-(3-chloro-2-pyridinyl)-1H-pyrazole-5-carbonyl chloride.

In a preferred embodiment the compounds of Formula (VII) is 2-amino-5-chloro-3-methylbenzoate.

In a preferred embodiment the compounds of Formula (VII) is methyl 2-amino-5-cyano-3-methylbenzoate.

In a preferred embodiment the compounds of Formula (VII) is methyl 2-amino-3-bromo-5-chlorobenzoate.

In an preferred embodiment alkyl amine of formula $(R_4)_q$—$NH_2$ is selected from 1-cyclopropyl ethylamine or methyl amine.

In a preferred embodiment the present invention provides a one pot process for the preparation of anthranilamides of Formula (IX) wherein said anthranilamide is chlorantraniliprole, cyantraniliprole or cyclaniliprole.

In a preferred embodiment the present invention provides a one pot process for the preparation of chlorantraniliprole wherein chlorantraniliprole is substantially free of certain impurities.

In another aspect the present invention provides a one pot process for the preparation of compound of Formula (XIII).

The one pot process for the preparation of compound of Formula (XIII) wherein Z is Cl and R' is $CH_3$ comprises: reacting compound of Formula (X) wherein Y is a halogen with a compound of Formula (XI) wherein Z is Cl and R is a lower alkyl group to obtain compound of Formula (XII)

wherein Z is Cl and reacting compound of Formula (XII) with alkyl amine of formula $R'NH_2$ to obtain compound of Formula (XIII) wherein Z is Cl and R' is $CH_3$.

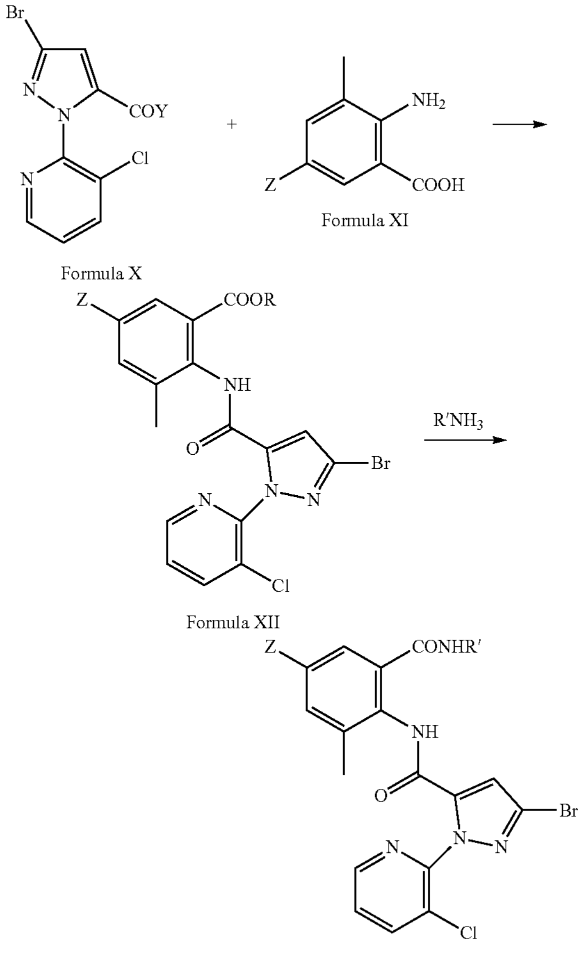

Formula X

Formula XI

Formula XII

Formula XIII

In an embodiment compound of Formula (XIII) is cyantraniliprole.

In an embodiment compound of Formula (XIII) is chlorantraniliprole.

In an embodiment the process for preparation of chlorantraniliprole of Formula (XIII) wherein Z is Cl and R' is $CH_3$ according to the present invention is performed in one pot.

In an embodiment the process is carried out in the absence of a base.

In an embodiment post-reaction treatment of Formula (XII) product is avoided.

In an embodiment the process is carried out at a temperature in the range of 30 to 120° C., preferably at a temperature range of 50 to 80° C.

In an embodiment Formula (XII) product is subjected to reaction with an $R'NH_2$ without isolation.

In an embodiment Formula (XII) product is subjected to reaction with methyl amine in the gaseous form or methyl amine as aqueous solution.

In an embodiment, reaction is carried out by purging methyl amine gas.

In an embodiment methyl amine gas is purged at a temperature range of 0 to 35° C., preferably at room temperature.

In an embodiment methyl amine gas is purged for 5 to 15 hours, preferably up to 8 hours.

In an embodiment the process is carried out in a polar organic solvent such as halogenated solvent, hydrocarbon solvent, ethers or acetonitrile.

In an embodiment the process is carried out in an organic solvent selected from halogenated hydrocarbon solvent, tetrahydrofuran or acetonitrile.

In an embodiment the preferred organic solvent is selected from dichloromethane, dichloroethane, tetrahydrofuran or acetonitrile.

In another embodiment the present invention provides a process for preparing chlorantraniliprole and said process comprising reaction of a compound of Formula (X) wherein Y is halogen, with a compound of Formula (XI) wherein R is $CH_3$ to obtain compound of Formula (XII) and further reacting the compound of Formula (XII) with methylamine gas to obtain chlorantraniliprole of Formula (XIII) wherein Z is Cl and R' is $CH_3$.

In an embodiment compound of Formula X wherein Y=a halogen; preferably chlorine.

In a preferred embodiment the present invention provides a one pot process for the preparation of chlorantraniliprole wherein chlorantraniliprole is substantially free of certain impurities.

In an embodiment compound of Formula (X) wherein Y is Cl is prepared by reacting compound of Formula (X) wherein Y is OH with a chlorinating agent selected from thionyl chloride, oxalyl chloride, phosphorus oxychloride, phosphorus trichloride or phosphorus pentachloride.

In an embodiment compound of Formula (XI) wherein R is $CH_3$ is prepared by reacting the corresponding acid with dimethyl sulfate.

The present invention further provides a one pot process for the preparation of cyantraniliprole of Formula (XIII) wherein Z is CN and R' is $CH_3$ said process comprising reaction of compound of Formula (X) wherein Y is a halogen, with a compound of Formula (XI) wherein Z is CN and R is a lower alkyl group to obtain compound of Formula (XII) wherein Z is CN; and reacting compound of Formula (XII) with methylamine to obtain said compound of Formula (XIII) wherein Z is CN and R' is $CH_3$.

In an embodiment the process for preparation of cyantraniliprole of Formula (XIII) wherein Z is CN and R' is $CH_3$ according to the present invention is a one pot process.

In an embodiment the reaction is carried out in the absence of a base.

In an embodiment post-reaction treatment of Formula (XII) compound is avoided.

In an embodiment Formula (XII) compound is subjected to reaction with an $R'NH_2$ without isolation.

In an embodiment Formula (XII) compound is subjected to reaction with methyl amine either in the gaseous form or as an aqueous solution.

In an embodiment, reaction is carried out by purging methyl amine gas.

In an embodiment the reaction is carried out in a polar organic solvent such as halogenated solvent, hydrocarbon solvent, ether or acetonitrile.

In an embodiment the reaction is carried out in an organic solvent selected from halogenated hydrocarbon solvent, tetrahydrofuran or acetonitrile.

In an embodiment the preferred organic solvent is selected from dichloromethane, dichloroethane, tetrahydrofuran or acetonitrile.

In an embodiment the present invention provides a process for preparing cyantraniliprole said process comprising reaction of a compound of Formula (X) with a compound of Formula (XI) wherein R is $CH_3$ in the absence of a base to obtain compound of Formula (XII) and further reacting compound of Formula (XII) with methylamine gas to obtain said cyantraniliprole.

In an embodiment compound of Formula (X) wherein Y is Cl is prepared by reacting compound of Formula (X) wherein Y is OH with a chlorinating agent selected from thionyl chloride, oxalyl chloride, phosphorus oxychloride, phosphorus trichloride or phosphorus pentachloride.

In an embodiment compound of Formula (XI) wherein R is $CH_3$ is prepared by reacting the corresponding acid with dimethyl sulfate.

The present invention further provides a process for the preparation of anthranilamides of Formula (XIII) said process comprising:

a) reacting compound of Formula (X) wherein Y is a halogen, with a compound of Formula XI wherein Z is halogen or —CN and R is a lower alkyl group, optionally in the presence of a weak base to obtain compound of Formula (XII), wherein Z and R has the same meaning as above; and
b) reacting compound of Formula (XII) with alkyl amine of formula $R'NH_2$ wherein said R' is selected from unsubstituted or substituted linear or branched ($C_1$-$C_{10}$) alkyl or cycloalkyl, heterocyclic unsubstituted or substituted with halogen, cyano, amino, hydorxyl or linear or branched ($C_1$-$C_{10}$) alkyl to obtain said compound of Formula (XIII).

The present invention further provides a process for the preparation of anthranilamides of Formula (XIII) in two steps wherein said reaction is carried out in the absence of a base.

In the context of the present invention, the term "optionally" when used in reference to any element; it is intended to mean that the reaction is carried out in presence of base or alternatively, is carried out in the absence of base. Both alternatives are intended to be within the scope of the present invention.

Thus, the present invention provides a process for the preparation of compound of Formula (XIII) wherein Z is Cl and R' is-$CH_3$ said process comprising the steps of:

1. reacting compound of Formula (X) wherein Y is halogen, with a compound of Formula (XI) wherein Z is Cl and R is a lower alkyl group to obtain compound of Formula (XII) wherein Z is Cl; and
2. reacting compound of Formula (XII) wherein Z is Cl with methylamine to obtain said compound of Formula (XIII) wherein Z is Cl and R' is $CH_3$.

wherein said process is carried out in the absence of a base.

In an embodiment the process is carried out in an organic solvent such as halogenated solvents, hydrocarbon solvents, ethers or acetonitrile.

The solvent used is selected from halogenated solvent such as dichloromethane, 4-bromotoluene, diiodomethane, carbon tetrachloride, chlorobenzene and chloroform; ketone such as acetone; a hydrocarbon solvent such as toluene, xylene and benzene, an ether solvent such as tetrahydrofuran, cyclopentyl methyl ether, 2-methyltetrahydrofuran, diethyl ether, dioxane, 1,4-dioxane, 1,2-dioxane and 1,3-dioxane or a mixture thereof.

In an embodiment the preferred organic solvent is selected from dichloromethane, dichloroethane, tetrahydrofuran or acetonitrile.

The present invention further provides a process for the preparation of anthranilamides of Formula (XIII) in two steps wherein step 1) of the reaction is carried out in the presence of weak base.

In an embodiment reaction of step 1) is carried out using a compound of Formula (X) wherein Y is halogen selected from chlorine or bromine.

In an embodiment reaction of step 1) is carried out using a compound of Formula (X) wherein Y is chlorine.

In an embodiment reaction of step 1) is carried out using a compound of Formula (XI) wherein Z is halogen selected from chlorine or bromine.

In an embodiment reaction of step 1) is carried out using a compound of Formula (XI) wherein Z is chlorine.

In an embodiment reaction of step 1 is carried out using a compound of Formula (XI) wherein Z is —CN.

In an embodiment step 1) of the reaction is carried out optionally using a weak base, preferably an inorganic weak base.

In an embodiment step 1) of the reaction is carried out in presence of base such as alkali or alkaline earth metal salts.

In an embodiment step 1) of the reaction is carried out in presence of base such as alkali or alkaline earth metal carbonates.

In an embodiment step 1) of the reaction is carried out in presence of base such as sodium carbonate or potassium carbonate.

In an embodiment step 2) of the reaction is carried out using compound of Formula (XII) with an alkyl amine wherein said alkyl group is selected from unsubstituted or substituted linear or branched ($C_1$-$C_{10}$)alkyl or cycloalkyl, heterocyclic unsubstituted or substituted with halogen, cyano, amino, hydroxyl or linear or branched ($C_1$-$C_{10}$) alkyl.

In a preferred embodiment step 2) of the reaction is carried out using compound of Formula (XII) with an alkyl amine wherein said alkyl group is an unsubstituted or substituted linear or branched ($C_1$-$C_{10}$)alkyl or cycloalkyl group.

In an embodiment the reaction is carried out in an organic solvent such as halogenated solvents, hydrocarbon solvents, ethers or acetonitrile.

In an embodiment the preferred organic solvent is selected from dichloromethane, dichloroethane, tetrahydrofuran or acetonitrile.

In a preferred embodiment compound of Formula (X), wherein Y is chlorine.

In a preferred embodiment compound of Formula (XI), wherein Z is chlorine and R is $CH_3$.

In a preferred embodiment the present invention provides a process for preparing Formula (XIII) said process involve reaction of a compound of Formula (X) wherein Y is chlorine with a compound of Formula (XI) wherein Z is chlorine and R is $CH_3$ using a weak base in a solvent to obtain compound of Formula (XII) and further reacting compound of Formula (XII) with methylamine in an organic solvent to obtain said compound of Formula (XIII).

In the present process the compounds of Formula (X) and Formula (XI) are prepared by methods known in the art.

The present invention provides a process for the preparation of chlorantraniliprole of Formula (XIII) wherein Z is Cl and R' is $CH_3$ said process comprising the steps of:

1) reacting compound of Formula (X) wherein Y is a halogen, with a compound of Formula (XI) wherein Z is Cl and R is a lower alkyl group optionally in the presence of a weak base to obtain compound of Formula (XII) wherein Z is Cl; and 2) reacting the compound of Formula (XII) wherein Z is Cl with methylamine to obtain said compound of Formula (IX) wherein Z is Cl and R' is $CH_3$.

In an embodiment step 1) of the process is carried out optionally using a weak base.

In an embodiment step 1) of the process is carried out using a weak inorganic base such as alkali or alkaline earth metal salts.

In an embodiment step 1) of the process is carried out using a base such as sodium carbonate or potassium carbonate.

In an embodiment step 1) of the process is carried out in a solvent preferably a polar organic solvent.

In an embodiment step 1) of the process is carryout in a solvent selected from halogenated hydrocarbon solvent, tetrahydrofuran or acetonitrile.

In an embodiment step 1) of the process is carried out in halogenated hydrocarbon solvent.

In an embodiment step 2) of the process is carried out in an organic solvent.

In an embodiment step 2) of the process is carried out in a solvent such as halogenated hydrocarbon solvents, tetrahydrofuran or acetonitrile.

In an embodiment, step 2) of the process is carried out by purging methyl amine gas.

In an embodiment, step 2) of the process is carried out by using methyl amine aqueous solution.

In a preferred embodiment the present invention provides a process for preparing chlorantraniliprole said process comprising reaction of a compound of Formula (X) wherein Y is Cl with a compound of Formula (XI) wherein Z is Cl and R is $CH_3$ using a weak base to obtain compound of Formula (XII) and further reacting compound of Formula (XII) with methylamine to obtain chlorantraniliprole.

In an embodiment the present process provides pure chlorantraniliprole wherein the purity of chlorantraniliprole is more than 95%.

In an embodiment the present invention provides chlorantraniliprole having purity at least 95% preferably at least 96% more preferably at least 97% by HPLC analysis.

In an embodiment the present invention provides chlorantraniliprole having purity at least 95% by HPLC analysis.

In an embodiment the present invention provides highly pure chlorantraniliprole or cyantraniliprole having purity of at least 95% by HPLC.

The present invention further provides a process for the preparation of cyantraniliprole of Formula (XIII) wherein Z is CN and R' is $CH_3$ and said process comprising:

a) reacting compound of Formula (X) wherein Y is a halogen, with a compound of Formula (XI) wherein Z is CN and R is a lower alkyl group optionally in the presence of a weak base to obtain compound of Formula (XII) wherein Z is CN; and
b) reacting compound of Formula (XII) with methylamine to obtain said compound of Formula (XIII) wherein Z is CN and R' is $CH_3$.

The advantages of the present invention are:

a) The reaction is carried out in one pot without the isolation of intermediates
b) One pot process reduces waste generation and effluents
c) Avoiding use of hazardous chemicals such as sulfonyl chlorides makes the isolation and purification process easier.
d) The process is economically advantageous and commercially viable.

Advantageously, the above identified elements of the process of the instant invention effectively contribute to the reduction of overall cost of the process. The present inventors also envisage that these synthetic efforts could be of value in producing a variety of anthranilamide compounds.

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present invention.

Example 1: Preparation of Chlorantraniliprole in the Absence of Base (One Pot Process)

A reaction kettle was charged with a solution of methyl 2-amino-5-chloro-3-methylbenzoate (502 gm) in dichloroethane (4663 gm). A solution of 3-Bromo-1-(3-chloro-2-pyridinyl)-1H-pyrazole-5-carbonyl chloride in dichloroethane (35%, 2350 gm) was added to the solution under stirring at 65-70° C. with nitrogen purging. Stirring was continued until completion of the reaction. The reaction mixture was then cooled to 25-30° C. and then purged with methylamine gas (20 gm) for about 5-7 hours. After completion of reaction the reaction mass was cooled to 0-5° C. followed by filtration. The wet cake (1175 gms) thus obtained was treated with 3% sodium hydroxide solution (1200 gms), filtered and washed with water (1000 gms) and dried to obtain title compound (940 gms); Purity: 97.4% by HPLC.

Example 2: Process for the Preparation of Chlorantraniliprole

A: Preparation of 3-Bromo-1-(3-chloro-2-pyridinyl)-1H-pyrazole-5-carbonyl chloride 3-bromo-1-(3-chloropyridin-2-yl)-1H-pyrazole-5-carboxylic acid (1942 g), dimethyl formamide (17 g), and dichloroethane (15000 g) were charged in a reaction kettle. Thionyl chloride (1047 g) was added dropwise to the reaction mixture under nitrogen atmosphere. The reaction mixture was then heated to 70-75° C. under stirring for 2-3 hrs. After completion of the reaction, the solvent was partially distilled out to get of 3-bromo-1-(3-chloropyridin-2-yl)-1H-pyrazole-5-carboxylic acid chloride (35% solution, 5770 gms), Purity: 97.18% by HPLC.

B: Preparation of Methyl 2-amino-5-chloro-3-methylbenzoate 2-amino-5-chloro-3-methylbenzoic acid (882 g), dimethyl formamide (4900 ml), and potassium carbonate (714 g) were charged into a reaction kettle and heated to 45-50° C. under stirring. Dimethyl sulfate (847 g) was added in 2 hrs at 45-50° C. and the reaction mass was heated to 70° C. and stirred for additional 2-3 hours. After completion of the reaction, the reaction mixture was cooled, filtered and the wet cake was washed with dimethyl formamide.

Dimethyl formamide from the filtrate was recovered under vacuum (755 mm/Hg) at 80-85° C.

Dichloroethane (3400) was then added to the residual mass followed by the addition of water (2600 gms) and stirred for one hour. Organic layer was separated and washed with water (900 gms). The solvent was removed by distillation to get Methyl 2-amino-5-chloro-3-methylbenzoate (855 gms), Purity: 97.7% by HPLC.

C: Preparation of 2-[[[3-bromo-1-(3-chloro-2-pyridinyl)-1H-pyrazol-5-yl]carbonyl]amino]-5-chloro-3-methyl-, Benzoic Acid, Methyl Ester Using Potassium Carbonate ($K_2CO_3$) as a Base A reaction kettle was charged with a solution of Methyl 2-amino-5-chloro-3-methylbenzoate (855 gm) in dichloroethane (3500 gm). $K_2CO_3$ (688 gm) was added into reaction kettle under stirring. A 35% solution of 3-Bromo-1-(3-chloro-2-pyridinyl)-1H-pyrazole-5-carbonyl chloride in dichloroethane (5770 gm) was added to the mixture in 6-7 hrs under nitrogen atm. and stirred until the completion of reaction. Water was then added to the reaction mass and organic layer was separated from the aqueous layer. The organic layer was washed with dilute caustic solution (2500 g; ~5%) and finally with water (1700 g). Solvent was evaporated from the organic layer at 60-65° C. under 740 mm/Hg vacuum to get 2-[[[3-bromo-1-(3-chloro-2-pyridinyl)-1H-pyrazol-5-yl]carbonyl]amino]-5-chloro-3-methyl-, Benzoic acid, methyl ester (2260 gm), Purity: 81.4% by HPLC.

D: Preparation of Chlorantraniliprole Using 40% Aqueous Solution of Methyl Amine A reaction kettle was charged with 2-[[[3-bromo-1-(3-chloro-2-pyridinyl)-1H-pyrazol-5-yl]carbonyl]amino]-5-chloro-3-methyl-, benzoic acid, methyl ester (2260 gm) and THF (7925 gm). 40% aqueous solution of methyl amine (2077 gm) was added to the kettle in 2 hrs and stirred for 6-7 hrs. After the completion of the reaction, THF was recovered and ethyl acetate (9000 gm) was added to the reaction mass and the mixture was heated to 70-75° C. under stirring. The mixture was then cooled to 25-30° C. and filtered, and the cake was washed with hot water. The mass was then dried to get 3-bromo-N-[4-chloro-2-methyl-6-[(methylamino) carbonyl]phenyl]-1-(3-chloro-2-pyridinyl)-1H-pyrazole-5-carboxamide (1000 g); Purity 97.1% by HPLC.

Example 3: Process for the Preparation of Chlorantraniliprole

A: Preparation of 2-[[[3-bromo-1-(3-chloro-2-pyridinyl)-1H-pyrazol-5-yl]carbonyl]amino]-5-chloro-3-methyl-, Benzoic Acid, Methyl Ester in the Absence of a Base A reaction kettle was charged with a solution of methyl 2-amino-5-chloro-3-methylbenzoate (502 Kg) in dichloroethane (5165 Kg). A 35% solution of 3-Bromo-1-(3-chloro-2-pyridinyl)-1H-pyrazole-5-carbonyl chloride in dichloroethane (2350 Kg) was added to the mixture in 6-7 hrs at 70-75° C. under nitrogen atm. and stirred until the completion of reaction. Water (220 Kg) was then added to the reaction mass and organic layer was separated from the aqueous layer. The separated organic layer was washed with dilute caustic solution (–5%) and finally with water (1700 g). Solvent was evaporated from the organic layer at 60-65° C. under 740 mm/Hg vacuum to get 2-[[3-bromo-1-(3-chloro-2-pyridinyl)-1H-pyrazol-5-yl]carbonylamino]-5-chloro-3-methyl-, Benzoic acid, methyl ester (7923 gm).

B: Preparation of Chlorantraniliprole

A reaction kettle was charged with 2-[[3-bromo-1-(3-chloro-2-pyridinyl)-1H-pyrazol-5-yl]carbonylamino]-5-chloro-3-methyl-, benzoic acid, methyl ester and dichloroethane (7923 Kg). The reaction mixture was then cooled to 25-30° C. and then purged with methyl amine gas (757 Kg) for about 5-7 hours. After completion of reaction the reaction mass was cooled to 0-5° C. followed by filtration. The wet cake thus obtained was treated with 3% sodium hydroxide solution (1000 Kg), filtered and washed with water (1000 gms) and dried to get the title product (1000 Kg). Purity: 97% by HPLC.

Example 4: One Pot Process for the Preparation of Cyantraniliprole in the Absence of Base A reaction kettle was charged with a solution of methyl 2-amino-5-cyano-3-methylbenzoate (476 gm) in dichloroethane (4663 gm). A solution of 3-Bromo-1-(3-chloro-2-pyridinyl)-1H-pyrazole-5-carbonyl chloride in dichloroethane (35%, 2350 gm) was added to the solution under stirring at 65-70° C. with nitrogen purging. Stirring was continued until completion of the reaction. The reaction mixture was then cooled to 25-30° C. and then purged with methyl amine gas (602 gm) for about 5-7 hours. After completion of reaction the reaction mass was cooled to 0-5° C. followed by filtration. The wet cake (1148 gms) as obtained was then treated with 3% sodium hydroxide solution (1150 gms), filtered and washed with water (1000 gms) and then dried. (922 gms); Purity: 95.1% by HPLC Example 5: One Pot Process for the Preparation of Cyclaniliprole in the Absence of Base A reaction kettle was charged with a solution of methyl 2-amino-3-bromo-5-chlorobenzoate (665 gm) in dichloroethane (4663 gm). A solution of 3-Bromo-1-(3-chloro-2-pyridinyl)-1H-pyrazole-5-carbonyl chloride in dichloroethane (35%, 2350 gm) was added to the solution under stirring at 65-70° C. with nitrogen purging. Stirring was continued until completion of the reaction. The reaction mixture was then cooled to 25-30° C. and then added 1-cyclopropylethylamine (470 gm) during 5-7 hours. After completion of reaction the reaction mass was cooled to 0-5° C. followed by filtration. The wet cake (1342 gms) as obtained was then treated with 3% sodium hydroxide solution (950 gms), filtered and washed with water (1000 gms) and then dried. (1168 gms); Purity: 95.6% by HPLC

We claim:

1. A process comprising preparation of anthranilamide compounds of Formula IX

Formula IX

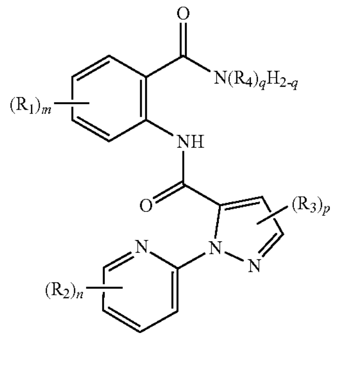

wherein the process is a one pot process having the steps of:

a) reacting compound of formula (VI) with a compound of Formula (VII) to obtain compound of Formula (VIII);

b) reacting compound of Formula (VIII) with an alkyl amine of Formula $(R_4)_q$—$NH_{2-q}$ to obtain a compound of Formula (IX);

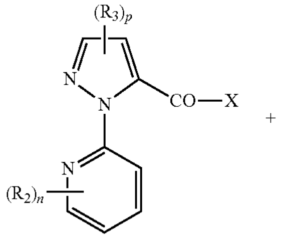

Formula VI

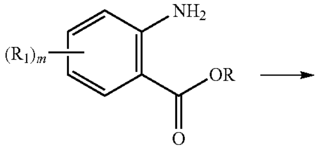

Formula VII

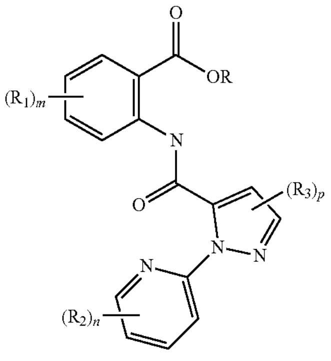

Formula VIII

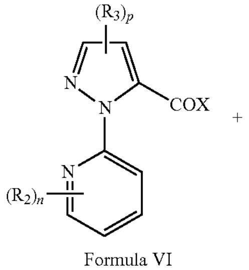

Formula VI

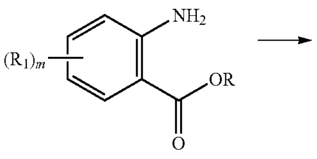

Formula VII

-continued

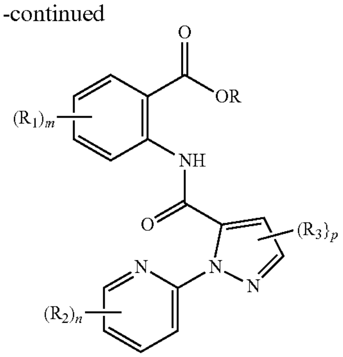

Formula VIII wherein X=a leaving group;

R=a lower alkyl group;

$R_1$ is a lower alkyl, halogen or cyano, $R_2$ is halogen, $R_3$ is halogen, $R_4$ is a lower alkyl or alkyl cycloalkyl, m is 2, n, p and q are each 1;

wherein said process is a one pot process and performed without isolating the compound of Formula (VIII).

2. The process of claim 1, wherein $R_1$ is $CH_3$, chlorine, bromine or cyano, $R_2$ is bromine, and $R_4$ is $CH_3$ or 1-cyclopropyl ethyl.

3. The process of claim 1, wherein said compound of Formula (IX) is chlorantraniliprole, cyclaniliprole or cyantraniliprole.

4. The process of claim 1 wherein said step a) is performed optionally in the presence of a weak base.

5. The process of claim 4, wherein said weak base is selected from alkali or alkaline earth metal carbonates.

6. The process of claim 1, wherein said step a) is performed in the absence of a base.

7. The process of claim 1, wherein said step a) is carried out at a temperature in the range from 30° C. to 120° C.

8. The process of claim 1, wherein said alkyl amine is methyl amine.

9. The process of claim 1, wherein said process is carried out in the presence of an organic solvent selected from halogenated solvent, hydrocarbon solvent, ether, acetonitrile or mixtures thereof.

10. The process of claim 9, wherein said process is carried out in the presence of an organic solvent selected from dichloromethane, dichloroethane, tetrahydrofuran, or acetonitrile.

* * * * *